United States Patent
Portney

[19]

[11] Patent Number: 6,132,436
[45] Date of Patent: Oct. 17, 2000

[54] SELF-REGULATING PHACO SLEEVE TO REDUCE TISSUE BURN

[75] Inventor: Valdemar Portney, Tustin, Calif.

[73] Assignee: Allergan, Irvine, Calif.

[21] Appl. No.: 09/118,492

[22] Filed: Jul. 17, 1998

[51] Int. Cl.[7] .................................................. A61B 1/30
[52] U.S. Cl. ........................... 606/107; 604/22; 604/272
[58] Field of Search .......................... 601/22, 272, 192, 601/2; 606/27, 107, 169

[56] References Cited

U.S. PATENT DOCUMENTS

| | | | |
|---|---|---|---|
| 4,530,356 | 7/1985 | Helfgott et al. | 128/305 |
| 4,681,102 | 7/1987 | Bartell | 128/303 R |
| 4,731,085 | 3/1988 | Koch | 623/16 |
| 4,787,889 | 11/1988 | Steppe et al. | 604/22 |
| 4,808,154 | 2/1989 | Freeman | 604/22 |
| 4,897,079 | 1/1990 | Zalfski et al. | 604/22 |
| 4,909,249 | 3/1990 | Akkas et al. | 606/107 |
| 4,940,468 | 7/1990 | Petillo | 606/170 |
| 4,983,160 | 1/1991 | Steppe et al. | 604/22 |
| 4,986,827 | 1/1991 | Akkas et al. | 606/107 |
| 5,019,035 | 5/1991 | Missirlian et al. | 604/22 |
| 5,026,393 | 6/1991 | Mackool | 623/6 |
| 5,059,204 | 10/1991 | Lawson et al. | 606/171 |
| 5,084,009 | 1/1992 | Mackool | 604/22 |
| 5,213,569 | 5/1993 | Davis | 604/22 |
| 5,257,988 | 11/1993 | L'Esperance | 606/6 |
| 5,282,786 | 2/1994 | Ureche | 604/22 |
| 5,286,256 | 2/1994 | Mackool | 604/22 |
| 5,354,265 | 10/1994 | Mackool | 604/22 |
| 5,496,342 | 3/1996 | Urich | 606/169 |
| 5,505,693 | 4/1996 | Mackool | 604/22 |
| 5,569,188 | 10/1996 | Mackool | 604/67 |
| 5,634,912 | 6/1997 | Injev | 604/264 |
| 5,645,530 | 7/1997 | Boukhny et al. | 604/22 |
| 5,667,489 | 9/1997 | Kraff et al. | 604/22 |
| 5,685,841 | 11/1997 | Mackool | 604/22 |
| 5,743,871 | 4/1998 | Strukel et al. | 604/35 |
| 5,807,310 | 9/1998 | Hood | 604/22 |
| 5,941,887 | 8/1999 | Steen et al. | 606/107 |
| 5,984,904 | 11/1999 | Steen et al. | 604/264 |
| 5,989,209 | 11/1999 | Barrett | 604/22 |
| 6,013,046 | 1/2000 | Maaskamp et al. | 604/22 |
| 6,042,586 | 3/2000 | Kawano et al. | 606/107 |

FOREIGN PATENT DOCUMENTS

| | | |
|---|---|---|
| WO 9607377 | 3/1996 | WIPO. |
| WO 9825542 | 6/1998 | WIPO. |

*Primary Examiner*—John P. Leubecker
*Assistant Examiner*—David M. Ruddy
*Attorney, Agent, or Firm*—Walter A. Hackler

[57] ABSTRACT

The sleeve apparatus for a phacoemulsification/irrigation and aspiration handpiece having an ultrasonic drive assembly attached to a hollow needle includes a compressible sleeve for establishing an annular passage around the needle and enabling the irrigation fluid to pass into an eye through a cornea/sclera wound while cooling the needle. The heat activated element is provided and disposed between the compressible sleeve and the needle for preventing contact between the compressible sleeve and the needle and maintaining the annular passage therebetween for irrigation fluid flow.

21 Claims, 1 Drawing Sheet

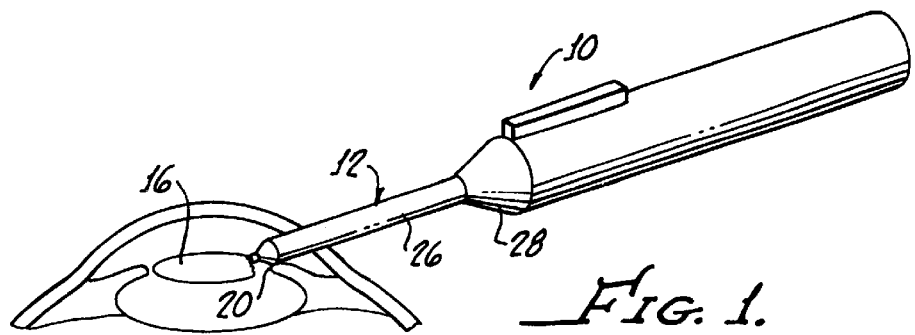
FIG. 1.
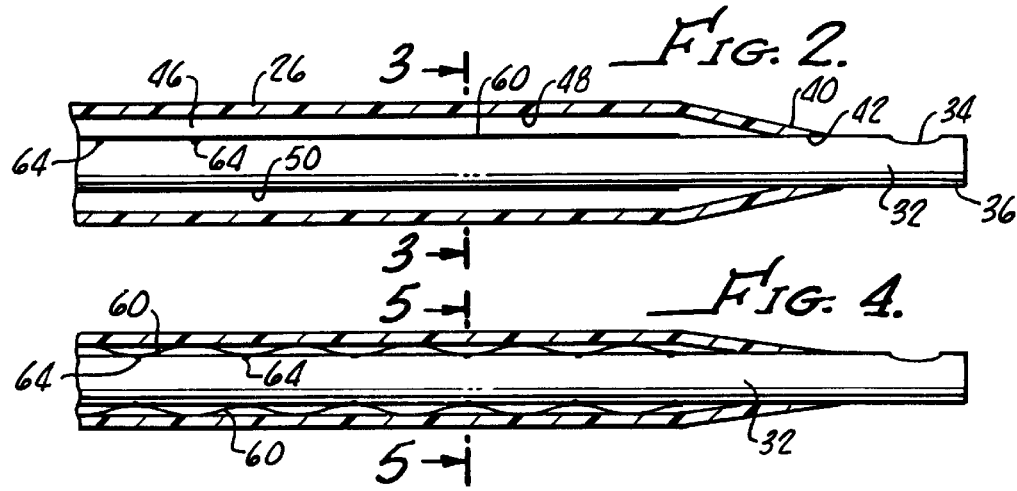
FIG. 2.
FIG. 4.
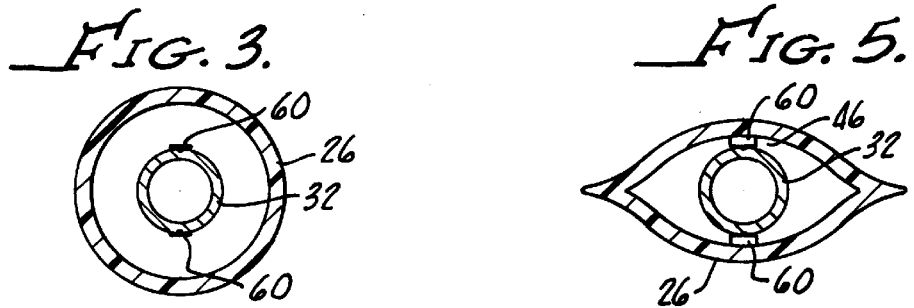
FIG. 3.
FIG. 5.
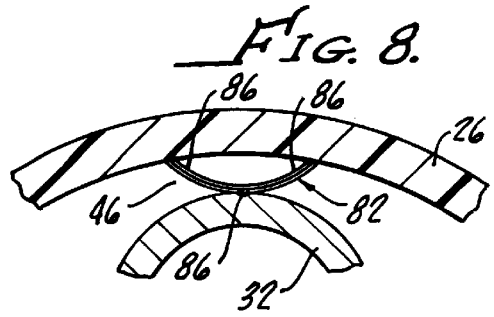
FIG. 6.
FIG. 8.
FIG. 7.

SELF-REGULATING PHACO SLEEVE TO REDUCE TISSUE BURN

The present invention generally relates to phacoemulsification handpieces for the removal of a cataract lens from an eye and is more particularly related to sleeve apparatus for a phacoemulsification handpiece.

A well known method for the removal of a cataract through a surgical incision in the eye is known as phacoemulsification. A handpiece for phacoemulsification generally includes an ultrasonic generator which is attached to a hollow needle which is vibrated and, when inserted into an eye, is capable of the emulsion of an eye lens and aspiration thereof through a lumen in the needle. The needle is surrounded by a sleeve when inserted through an incision in the eye. The tip of the needle engages and emulsifies the cataract and a suction force is applied through the needle interior lumen to withdraw the emulsified cataract into the needle and out of the eye.

The sleeve protects the wound through which the needle is passed from contacting the needle which can become heated and the sleeve further establishes an annular passage around the needle for providing an irrigation fluid to the eye while at the same time cooling the needle.

Typically, the cornea or sclera incision is linear and has a length approximately to one-half the circumference of the sleeve in order to minimize fluid leakage from the incision, or wound, when the needle/sleeve is inserted therethrough.

A great number of sleeve designs have been proposed and a number of materials have been utilized in prior art sleeves. For example, U.S. Pat. No. 4,787,889 to Steppe et al, discloses a flexible sleeve made of a synthetic resin such as silicon rubber which is able to fold back or telescope when inserted through an incision. The problems with these prior art devices include collapsing of the flexible sleeve in the area of the wound by pressure from surrounding tissue. This collapsing of the sleeve blocks flow of the irrigation to the surgical site and around the vibrating needle, which can cause overheating and damage to adjacent tissue. Sleeves made out of metallic material, such as also described in the hereinabove referenced U.S. patent, do not allow collapse and, accordingly, allow a greater fluid leakage from the wound.

In order to minimize leakage from the wound past the sleeve and the elliptical sleeve has been proposed, for example, see U.S. Pat. No. 5,084,009. This collapsible, or compressible, sleeve is made with a shape matching the configuration of a surgical incision in order to minimize leakage between the exterior surface of the sleeve and the surgical incision. However, in order for the ultrasonic needle to exhibit a desired and vibratory motion, which is relatively free from damping, this rounding sleeve must be prohibited from touching the needle during the operation.

During operation procedures, the needle must be partially rotated and its angle of incident changed in order to effect complete phacoemulsification and movement of the lens. In these procedures, a soft sleeve, particularly one shaped to the size of the wound, may collapse, or deflect against the ultrasonic needle. When the sleeve is pushed against the rapidly vibrating needle, the needle and sleeve tend to overheat due to friction, which may damage delicate cornea or sclera tissue, particularly the corneal epithelium.

The present invention is directed to a sleeve which, in response to needle temperature, self-regulates in order to maintain proper annular channel around the needle for passage of cooling fluid and prevent the needle from touching the sleeve.

SUMMARY OF THE INVENTION

The sleeve apparatus in accordance with the present invention for a phacoemulsification/irrigation and aspiration handpiece generally includes a compressible sleeve which provides a means for establishing an annular passage around a needle of the handpiece and enabling irrigation fluid to pass into an eye through a cornea/sclera wound while at the same time cooling the needle. In combination therewith, heat activated means are provided and disposed between the compressible sleeve and the needle for preventing contact between the compressible sleeve means and the needle and maintaining the annular passage for irrigation fluid flow.

In this regard, the heat activated means is heat sensitive for controlling a size of the annular passage in response to needle temperature. Accordingly, the heat sensitive means is self-regulating for maintaining the annular passage around the needle in order to reduce incidence of cornea/sclera tissue burn.

More particularly, the heat activated means may comprise a bimetallic element or spring. In one embodiment, the bimetallic spring includes a U-shaped element fixed to the needle with movable arms extending therefrom. Two bimetallic springs may be provided which are oriented within the annular passage at 108° angular relationship from one another.

It is to be appreciated that the heat-activated means may include any heat expandable element and in another embodiment of the present invention, the heat expandable element may be disposed longitudinally along the needle.

BRIEF DESCRIPTION OF THE DRAWINGS

The present invention may be more clearly appreciated when taken in conjunction with the accompanying drawings, in which:

FIG. 1 is a perspective view of a phacoemulsification handpiece utilizing the sleeve apparatus in accordance with the present invention as it may be inserted through a cornea/sclera wound with the removal of a cataract lens from a lens capsule;

FIG. 2 is a cross sectional view of one embodiment of sleeve apparatus in accordance with the present invention which includes a compressible sleeve and a heat expandable element attached to a needle within the sleeve which, being heat activated, prevents contact between the compressible sleeve and the needle in order to maintain an annular passage for irrigation fluid flow;

FIG. 3 is a cross section taken along the line 3—3 of FIG. 2 showing the heat expandable element in unexpanded state and disposed generally against the needle;

FIG. 4 is a cross sectional view corresponding to FIG. 2 in which the activated means, or expandable element, is heated to cause a serpentine ribbon between the needle and the sleeve in order to prevent contact between the compressible sleeve and the needle;

FIG. 5 is a cross sectional view taken along the line 5—5 of FIG. 4 showing an expanded heat-activated element;

FIG. 6 is another embodiment in accordance with the present invention in which a plurality of U-shaped bimetallic springs are attached to the needle, which are heat-sensitive, and act to control the size of the annular passage between the needle and the sleeve as a function of needle temperature;

FIG. 7 is a cross-sectional view taken along the line 7—7 of FIG. 6 showing curved U-shaped bimetallic elements for maintaining the angular passage around the needle in order to reduce incidence of cornea/sclera tissue burn; and FIG. 8 is an enlarged view of the needle, sleeve and bimetallic element activated to maintain an annular passage between the needle and the sleeve.

DETAILED DESCRIPTION OF THE DRAWINGS

Turning now to FIG. 1, there is shown a phacoemulsification handpiece 10 utilizing sleeve apparatus 12 in accordance with the present invention for removing a cataract lens 16 by emulsification/aspiration through a corneal/sclera wound 20. The phaco handpiece, or instrument 10, may be of any conventional type operating, as is well known to those skilled in the art, except as modified with the sleeve apparatus 12 in accordance with the present invention. The sleeve apparatus 12 includes a sleeve 26 and a hub 28 fixed thereto.

It should be appreciated that the sleeve 26 and the hub 28 may be formed from the same type of material, for example, a silicone or a silicon-type material, or a thermoplastic polyurethane. Further the sleeve 26 and the hub may be inner fixed to one another or integrally formed.

The handpiece 10, includes an ultrasonic drive assembly, not shown, attached to a hollow needle 32, see FIG. 2, which includes at least one port 34 disposed in an end 36, a needle 32, the end 36 protruding through the sleeve 26 at a distal end 40 with a seal 42 disposed therebetween.

As shown in FIG. 2, an annular passage of 46 is established between an inside surface 48 of the sleeve 26 and an outside surface 50 of the needle 32 in order to enable irrigation fluid, provided by the handpiece, to pass around the needle 32 and through the port 34 in a conventional manner, the fluid inner connection between the annular passage 46 and the handpiece, is not shown, as this arrangement is well known in the art.

It is important that during a phacoemulsification procedure, tissue surrounding the cornea/sclera wound will not be damaged, particularly the epithelium layer under the cornea. Since damage to this tissue may occur due to heating, it is also important that the needle 32 not contact the sleeve 26 because conductive heat transfer to the tissue surrounding the wound 20 would cause undesired heating thereof.

Accordingly, heat activated means 60 disposed between the compressible sleeve 26 and the needle 32 is provided for preventing contact between the compressible sleeve 26 and the needle 32 and further maintaining an annular passage for irrigation fluid flow. This heat activated means comprises a heat sensitive element which may be metal but importantly has a greater coefficient of expansion than the needle 32. The element 60 is attached to the needle at various spaced apart points 64 so that upon heating of the needle 32, expansion of the elements 60 occurs as shown in FIG. 4.

Preferably, two or more of the elements are provided and preferably disposed in a uniformed angularly spaced apart relationship around the needle 32 and between the needle 32 and the sleeve 26 in order to maintain the annular passage 46.

FIG. 3 shows the element 60 attached to the needle in an unheated state and corresponding to FIG. 4, the cross section shown in FIG. 5 shows the element 60 expanded in order to prevent contact between the needle 32 and the sleeve 26.

As hereinabove noted, any suitable material may be utilized for the heat sensitive element 64 as long as an appropriate coefficient of expansion is selected. Accordingly, this material will depend upon the material of construction of the sleeve 32.

An alternative embodiment 80 of the present invention is shown in FIGS. 6–8. In this embodiment, a plurality of heat activated bimetallic springs 82 are attached to the needle 32 by spot welding or the like at a central point 86, see FIG. 8.

As shown in FIG. 6, these bimetallic springs lie relatively flat against the needle 32, but upon heating thereof by a rise of temperature, the needle 32, the heat sensitive, or activated springs 82, become U-shaped as shown in FIGS. 7 and 8. Essentially, the bimetallic springs have movable arms 86 extending and contacting the sleeve 26 as shown in FIGS. 7 and 8 in order to prevent contact between the compressible sleeve 26 and the needle 32 while maintaining an annular passage 46 for passage of the irrigation fluid.

It should be appreciated that any well known type of bimetallic element or combination of materials having different coefficient of expansions may be utilized in accordance with the present invention so that movement occurs in response to the heat generated by the needle 32 which may achieve temperatures in the order of about 50° C. during operation.

Although there has been hereinabove described specific embodiments of sleeve apparatus in accordance with the present invention, for the purpose of illustrating the manner to which the invention may be used to advantage, it should be appreciated that the invention is not limited thereto. Accordingly, any and all embodiments, variations, or equivalent arrangements which may occur to those skilled in the art, should be considered to be within the scope of the present invention as defined in the appended claims.

What is claimed is:

1. Sleeve apparatus for a phacoemulsification/irrigation and aspiration handpiece having an ultrasonic drive assembly attached to a hollow needle for emulsifying and aspirating a cataract lens through a cornea/sclera wound, said sleeve apparatus comprising:

compressible sleeve means for establishing an annular passage around the needle and enabling irrigation fluid to pass into an eye through the cornea/sclera wound while cooling the needle; and heat activated means, disposed between said compressible sleeve means and said needle, for preventing contact between said compressible sleeve means and said needle and maintaining the annular passage for irrigation fluid flow and wherein said heat activated means has a greater coefficient of expansion than the needle.

2. The sleeve apparatus according to claim 1 wherein said heat activated means comprises a bimetallic spring.

3. The sleeve apparatus according to claim 2 wherein said bimetallic spring comprises a U-shaped element fixed to said needle with movable arms extending therefrom.

4. The sleeve apparatus according to claim 1 wherein said heat activated means comprises two bimetallic springs oriented within said annular passage at 180° from one another.

5. The sleeve apparatus according to claim 4 wherein each of the two bimetallic springs are U-shaped elements fixed to said needle with movable arms extending therefrom.

6. The sleeve apparatus according to claim 1 wherein said heat activated means comprises a heat expandable element.

7. The sleeve apparatus according to claim 6 wherein said heat expandable element is disposed longitudinally along said needle.

8. Sleeve apparatus for a phacoemulsification/irrigation and aspiration handpiece having an ultrasonic drive assembly attached to a hollow needle for emulsifying and aspirating a cataract lens through a cornea/sclera wound, said sleeve apparatus comprising:

compressible sleeve means for establishing an annular passage around the needle and enabling irrigation fluid to pass into an eye through the cornea/sclera wound while cooling the needle, and heat sensitive, self-regulating means, disposed between said compressible sleeve means and said needle for maintaining the annular passage around the needle in order to reduce incidence of cornea/sclera tissue burn and wherein said heat sensitive, self-regulating means has a greater coefficient of expansion than the needle.

9. The sleeve apparatus according to claim 8 wherein said heat sensitive regulating means comprises a bimetallic spring.

10. The sleeve apparatus according to claim 9 wherein said bimetallic spring comprises a U-shaped element fixed to said needle with movable arms extending therefrom.

11. The sleeve apparatus according to claim 8 wherein said heat sensitive self-regulating means comprises two bimetallic springs oriented within said annular passage at 180° from one another.

12. The sleeve apparatus according to claim 11 wherein each of the two bimetallic springs are U-shaped elements fixed to said needle with movable arms extending therefrom.

13. The sleeve apparatus according to claim 8 wherein said heat sensitive self-regulating means comprises a heat expandable element.

14. The sleeve apparatus according to claim 13 wherein said heat expandable element is disposed longitudinally along said needle.

15. Sleeve apparatus for a phacoemulsification/irrigation and aspiration handpiece having an ultrasonic drive assembly attached to a hollow needle for emulsifying and aspirating a cataract lens through a cornea/sclera wound, said sleeve apparatus comprising:

compressible sleeve means for establishing an annular passage around said needle and enabling irrigation fluid to pass into an eye through the cornea/sclera wound while cooling the needle; and heat sensitive means, disposed between said compressible sleeve and said needle for controlling a size of said annular passage in response to needle temperature, the annular passage size being increased in response to increased needle temperature and wherein said heat sensitive means has a greater coefficient of expansion than the needle.

16. The sleeve apparatus according to claim 15 herein said heat sensitive means comprises a bimetallic spring.

17. The sleeve apparatus according to claim 16 wherein said bimetallic spring comprises a U-shaped element fixed to said needle with movable arms extending therefrom.

18. The sleeve apparatus according to claim 15 wherein said heat sensitive means comprises two bimetallic springs oriented within said annular passage at 180° from one another.

19. The sleeve apparatus according to claim 18 wherein each of the two bimetallic springs are U-shaped elements fixed to said needle with movable arms extending therefrom.

20. The sleeve apparatus according to claim 15 wherein said heat sensitive means comprises a heat expandable element.

21. The sleeve apparatus according to claim 20 wherein said heat expandable element is disposed longitudinally along said needle.

* * * * *